US00PP29317P3

(12) United States Plant Patent
Maillard et al.

(10) Patent No.: US PP29,317 P3
(45) Date of Patent: May 29, 2018

(54) CHERRY TREE NAMED 'REDLAM'

(50) Latin Name: ***Prunus avium* (L.) L.**
Varietal Denomination: REDLAM

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days. days.

(21) Appl. No.: 15/330,879

(22) Filed: Nov. 10, 2016

(65) Prior Publication Data

US 2017/0188495 P1 Jun. 29, 2017

(30) Foreign Application Priority Data

Nov. 27, 2015 (QZ) ..... PBR 2015/2856

(51) Int. Cl.
*A01H 5/08* (2018.01)

(52) U.S. Cl.
USPC ..... Plt./181
CPC ..... *A01H 5/085* (2013.01)

(58) Field of Classification Search
USPC ..... Plt./181
CPC ..... A01H 5/085
See application file for complete search history.

*Primary Examiner* — Kent L Bell
(74) *Attorney, Agent, or Firm* — Westerman, Hattori, Daniels & Adrian, LLP

(57) ABSTRACT

A new and distinct variety of cherry tree denominated 'REDLAM' has fruits with medium to large size and dark red skin color, very firm, and with a good flavor and eating quality; the fruit is further characterized by its good handling and storage qualities.

2 Drawing Sheets

Latin name of the genus and species of the plant claimed: *Prunus avium* (L.) L.

Variety denomination: 'REDLAM'.

This application claims priority of Community plant variety right No. 2015/2856 filed on Nov. 27, 2015 (Nov. 27, 2015) which is hereby incorporated by reference in its entirety.

BACKGROUND OF THE NEW VARIETY

Field of the Invention

In the field of plant genetics, we conduct an extensive and continuing plant-breeding program including the organization and reproduction of orchard trees, among which peaches, nectarines, apricots, apples, and cherries are exemplary. It was against this background of our activities that the present variety of cherry tree was originated and reproduced by us in our experimental orchard located near Elne, Pyrénées Orientales, France.

ORIGIN OF THE VARIETY

The present invention relates to a new a distinct variety of cherry tree *Prunus avium* L. which has been given the variety denomination 'REDLAM'. This tree produces fruits with a long shelf life without alteration both on the trees after growth completion and after harvesting, very good eating quality with an orange yellow flesh with a red pigmentation when fruits reach maturity, and for fresh market in May in the Pyrénées Orientales department, France.

Contrast is made to 'FOLFER' cherry tree (non patented) and to 'BURLAT' cherry tree (non patented) for reliable description. 'REDLAM' is a promising candidate for commercial success in that it produces very attractive fruits having a long shelf life.

The present new variety of cherry tree (*Prunus avium* L.) was developed by us in our experimental orchard located in France. 'REDLAM' cherry tree originated in a cultivated area of the South of France, in the Pyrénées-Orientales department where it was also tested. This zone also called Roussillon is subject to a Mediterranean climate. The winter is generally sweet that is to say the total amount of cold hours lower than 7° C. (Celsius) varies from 600 hours to 1200 hours. The summer is hot and dry. that is to say the total amount of sunshine hours is an average of 2400 hours to 2800 hours per year. The prevailing wind is called "Tramontane": it dries the air and clear the sky from cloud but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen and the summer is dry with a few thunderstorms.

The 'REDLAM' variety resulted from a pollinated cross between cherry tree variety named 'ASF 9904' (non patented and no longer in existence) which was used as the seed parent, and the 'ROSILAM' cherry tree (U.S. Plant Pat. No. 23,797), which was used as the pollen parent.

The cherry variety named 'ASF 9904' had been in existence only in the aim of being a parental variety. This variety had not been selected in order to produce fruits because of its lack of firmness and, finally, the 'ASF 9904' variety was not maintained.

The 'REDLAM' variety was obtained by hybridizing and propagated by grafting on a 'Maxma14' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 Elne, Pyrénées Orientales, France. More particularly, the plant was reproduced by grafting.

Compared to its male parent 'ROSILAM' variety (U.S. Plant Pat. No. 23,797), which is a two-colored cherry tree, the new variety 'REDLAM' is considered as a red cherry tree. The flowers of the new variety 'REDLAM' bloom approximately at the same time as the flowers of the variety named 'ROSILAM' or slightly earlier.

Regarding the ripening period, the fruits of the new variety 'REDLAM' ripen one to two weeks earlier than the fruits of the 'ROSILAM' variety.

For the new variety 'REDLAM', the color of the fruits is red (RHS RED PURPLE 187 B) on a dark red color background (RHS RED GROUP 46 A). In comparison, the 'ROSILAM' variety produces fruits that have an homogenous pink red color covering 50 to 60% of the fruit skin surface (RHS RED GROUP 46 A or RHS RED GROUP 46 B) on a shining creamy golden background covering 40 to 50% of the fruit skin surface.

Regarding the characteristic related to the stone size, the stone of the new variety 'REDLAM' is considered medium whereas the stone of 'ROSILAM' is small to medium.

The juice color of the new variety 'REDLAM' is pink red (RHS RED PURPLE 73 D) whereas the juice color of the parent variety 'ROSILAM' is colorless and sometimes slightly creamy (RHS YELLOW WHITE 158 B or RHS YELLOW WHITE 158 C or RHS YELLOW WHITE 158 D).

The color of the flesh of the new variety 'REDLAM' is considered orange yellow (RHS YELLOW ORANGE 14 D) and turns to a pigmented red color (RHS RED GROUP 53 B) at ripening time. In comparison, the flesh color of the 'ROSILAM' variety is creamy yellow (RHS YELLOW WHITE GROUP 158 B or RHS YELLOW WHITE GROUP 158 C)

SUMMARY OF THE NEW VARIETY

The new variety 'REDLAM' produces fruits of medium to large size, firm, with a semi-sweet flavor, low acidity, and an orange yellow color with a red pigmentation when mature. The blooming period is medium for the variety, namely at the beginning of April. The maturity period is early to medium, generally from the middle of May to beginning of June in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, in Elne, Pyrénées-Orientales department, South of France.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of cherry tree, its flowers, foliage and fruit, as based on observations of specimens grown near Elne, South of France, with color in accordance with The R.H.S. Color Chart (Fourth Edition) provided by The Royal Horticultural Society of Great Britain.

The trees, flowers and fruits may vary in slight detail due to variations in soil type, cultural practices and climatic conditions.

Figure 1:
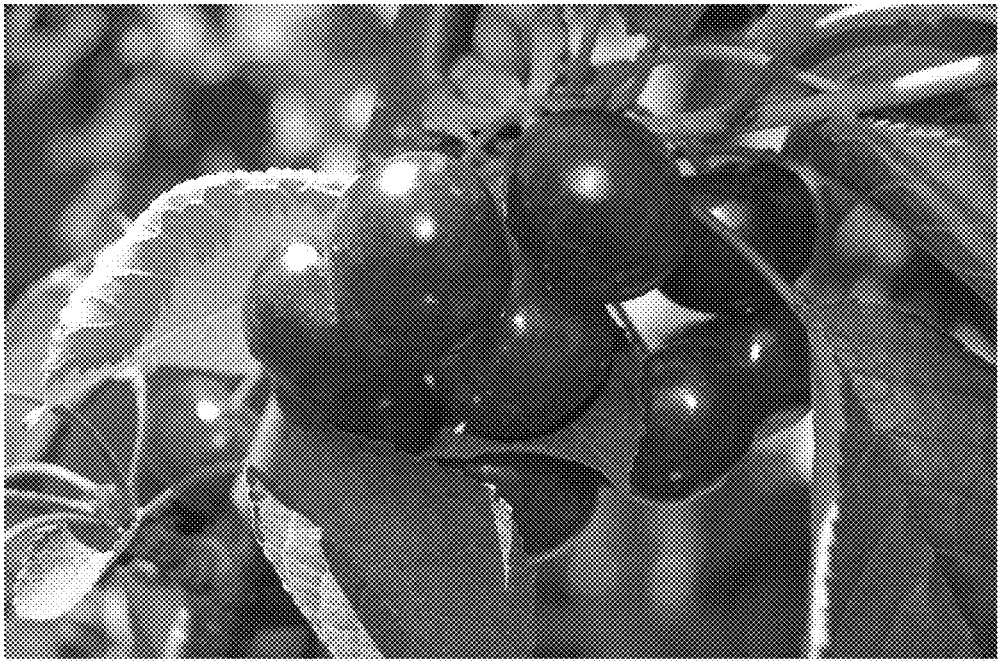
FIG. 1 is a color photograph which shows a view of a tree of the new variety in orchard, with branches bearing fruits.
Figure 2:
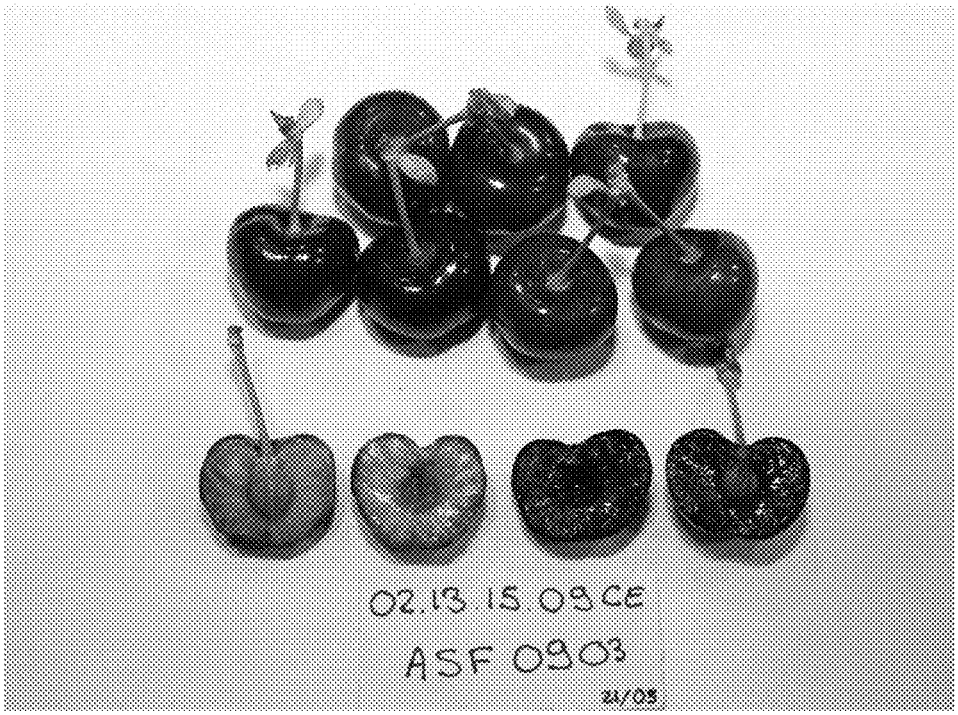
FIG. 2 is a color photograph which shows some whole fruits of the new variety, and two fruits at different maturity stages, having been cut in a half, with the stone being left in one of the halves, for depicting the fruit flesh, the pit, and the pit cavity of the new variety.
Figure 3:
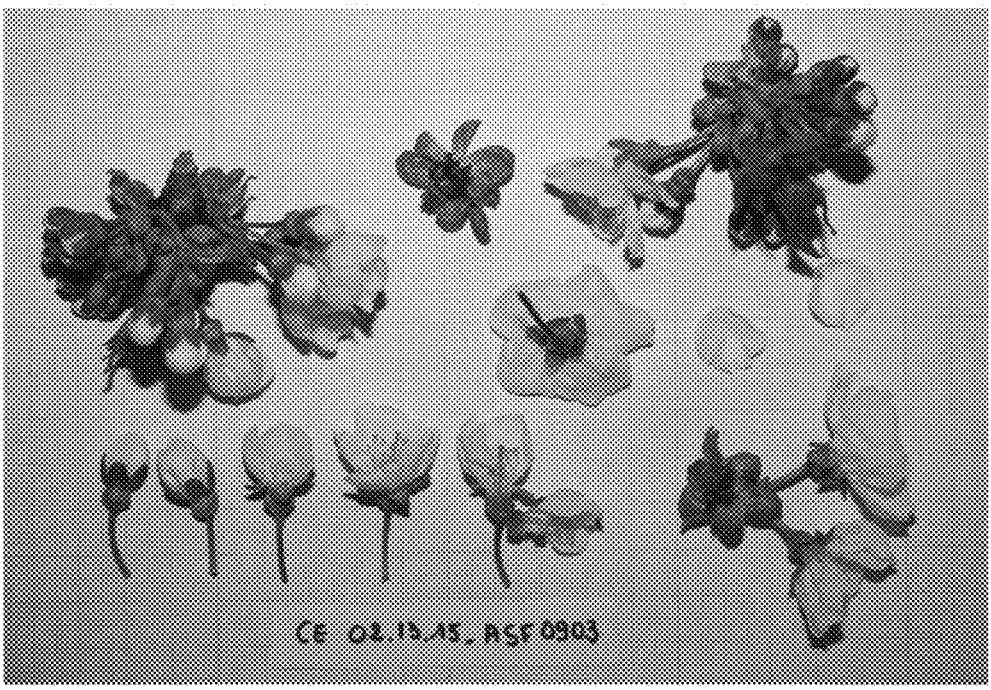
FIG. 3 shows typical white flowers of 'REDLAM' variety at blooming with some leaves for depicting the flower buds at different stages of development; and the reverse and side view of the flowers and the reproductive organs with petals removed, of the new variety.
Figure 4:
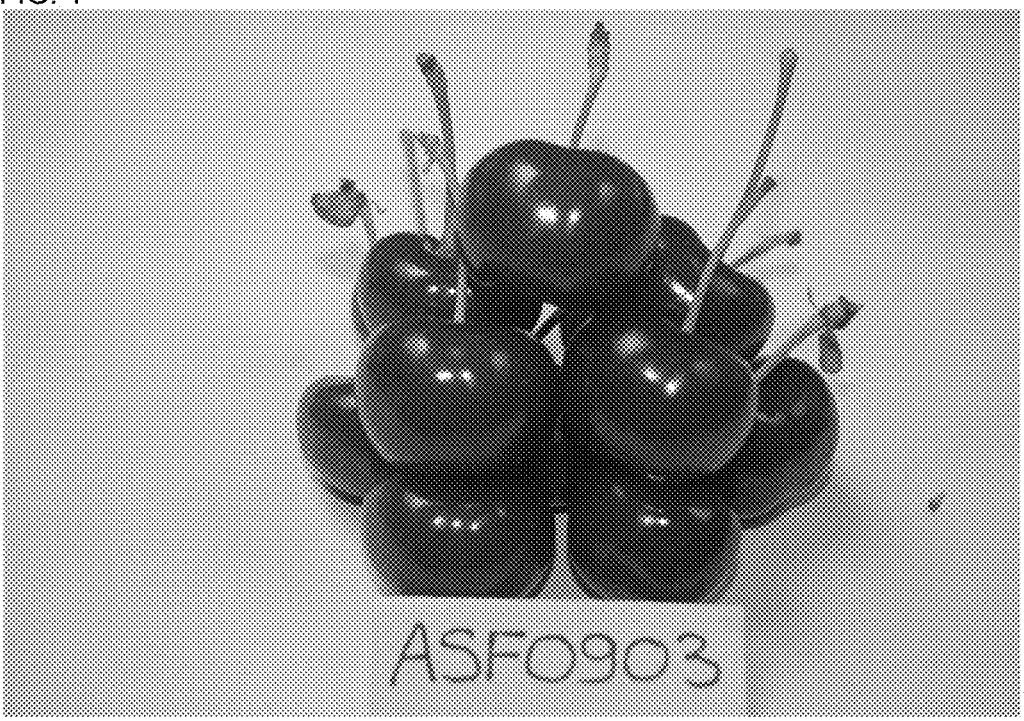
FIG. 4 is a color photograph that shows a close view of typical fruits of the new variety 'REDLAM' at ripening time.

The main characteristics of this new variety of sweet cherry are a medium or large fruit size with a color of skin considered red. The color of fruit flesh depends on the maturity stage of the fruit, as shown on the photography of FIG. 2. The fruit is very firm.

The time of beginning of flowering is medium whereas the time of beginning of fruit ripening is considered early to medium.

In comparison with the cherry tree 'FOLFER' (non-patented), the present variety 'REDLAM' ripens generally at the same time. The flavor of the variety named 'FOLFER' is considered sugary whereas the flavor of the new variety 'REDLAM' is very sugary, with a brix comprised between 16 and 18 degrees. Moreover, the 'FOLFER' variety is sensitive to cracking whereas the new variety 'REDLAM' is not sensitive to cracking.

Compared to 'BURLAT' (non patented) cherry tree, which produces fruits of about 8 grams, 'REDLAM' variety produces fruits that are more heavy, with a weight of approximately 11 to 12 grams and a bigger size. Indeed, the medium diameter of the 'REDLAM' fruits is about 30 millimeters.

DETAILED DESCRIPTION

Referring more specifically to the pomological details of this new and distinct variety of cherry tree, the following has been observed on trees on their fifth growing season (fourth year of production) under the ecological conditions prevailing at the orchards located near the town of Elne, Pyrénées-Orientales department, France.

All observations have been done on rootstock cultivar. The rootstock was a 'MAXMA14' tree. All major color code designations are by reference to The R.H.S. Colour Chart 2001 (Fourth Edition) provided by The Royal Horticultural Society of Great Britain.

Tree:

Generally: The first year the cherry tree is generally cut at 2.50 meters height. The length in one year for each lateral shoot varies from 0.60 meters to 0.80 meters. We are cutting the cherry trees during the second year to a height of 2.50 meters. The form of the cheery trees is cylindrical and the diameter is limited to 2 meters.

*Size*.—Medium to high as compared to other commercial sweet cherry cultivars. The tree size the first year was approximately 2.50 meters. The tree was pruned during each following dormant season to a height of approximately 2.50 meters. Current seasons shoots growth could reach 0.80 meters. So the tree size from the second year (second and next years) reached a final height of 3.10 to 3.30 meters with current seasons shoots length comprised. The mature branches have been pruned to a length of 30.0 centimeters in order to place nets on the trees.

*Spread*.—Approximately 2.0 meters with a cylindrical shape. The whole orchard was oriented to a central leader organization, with tree lines spaced of 4.0 meters and trees spaced of 1 meter in a same tree line.

*Vigor*.—Medium, tree growth reaching 0.60 to 0.80 meters the first growing season.

*Productivity*.—Good to very good productivity, every year. The new variety produces adequate fruit set annually on a regular basis. The number of the fruit set varies with the prevailing climatic conditions and cultivar practices employed during the bloom period, and is therefore not distinctive of the present variety. It is estimated that productivity is about 10 tons per hectare.

*Bearer*.—Very regular and quantitative. The extinction of the clusters of May improves the calibre and firmness of the fruit.

*Form*.—Naturally spreading to semi-upright.

*Hardiness*.—Hardy in all stone fruit growing areas of France and especially where the chilling requirement is between 350 and 1200 hours. No injury with a temperatures as low as −12° C. in winter. Good resistance to late frosts.

Trunk:

*Size*.—Medium. Approximately 82 millimeters above 20.0 centimeters from ground, on $5^{th}$ growing season.

*Bark texture*.—Smooth to rough, due to the lenticels.

*Lenticels*.—High number of lenticels. The number of lenticels reaches 28 to 32 lenticels per 10 $cm^2$. At the $5^{th}$ growing season, lenticels are 3.0 to 4.0 millimeters in height and 6.0 to 9.0 millimeters in width.

*Lenticels color*.—Color of lenticels is RHS GREYED ORANGE N167 D.

*Bark color*.—Grey silver brown (RHS Brown 200 B).

Branches:

*Size*.—Medium for the new growth, between 40.0 and 55.0 centimeters. Medium for the branches at the $5^{th}$ growing season.

*Diameter*.—Average diameter of 25.0 to 47.0 millimeters.

*Surface texture*.—Smooth to rough. Wood that is several years old has no furrowed appearance.

*Color*.—Old growth is brown (RHS Brown 200 B).

Current season shoots:

*Diameter*.—Average diameter from 7.0 to 8.0 millimeters.

*Surface texture*.—Smooth with lenticels. The number of lenticels reaches 28 to 32 lenticels per 10 $cm^2$. The lenticels are 3.0 to 4.0 millimeters in height and 6.0 to 9.0 millimeters in width. The color of the lenticels is RHS Greyed Orange N 167 D. Wood that is several years old has no furrowed appearance.

*Crotch angles*.—Primary branches are considered variable, but the crotch angles are generally between 65 degrees and 85 degrees from the horizontal axis. This particular characteristic is not considered distinctive of the variety, however.

*Internode*.—Generally from 55.0 millimeters to 65.0 millimeters length.

*Color*.—New growth is orange brown (RHS Greyed Orange 166 A).

Leaves:

*Size*.—Medium for the species. Leaf measurements have been taken from vigorous, upright, current-season growth at approximately mid-shoot. The ratio leaf length/leaf width is 2.14.

*Length*.—From 130.0 to 175.0 millimeters with leaf petiole. Average length with petiole 148.4 millimeters.

*Width*.—From 62.0 to 75.0 millimeters. Average width 69.2 millimeters.

*Leaf form in cross view*.—Concave.

*Leaf form*.—Lanceolate to spatulate (spoon-shaped) with an elliptic shape.

*Apex*.—Acuminate.

*Leaf base*.—Round.

Leaf color:

*Upper leaf surface*.—Dark green (RHS GREEN GROUP 137 B).

*Lower surface*.—A lighter green than the upper leaf surface (RHS YELLOW GREEN 146 B).

*Leaf texture*.—Smooth. The lower surface is also smooth.

*Leaf venation*.—Pinnately veined.

Mid-vein:

*Color*.—Light green with a yellow touch (RHS YELLOW GREEN 145 B to RHS YELLOW GREEN 145 C) and evolves with maturity.

*Leaf margins*.—Undulating.

*Form*.—Considered dentate.

*Uniformity*.—Leaves are identical.

Leaf petioles:

*Size*.—Considered short.

*Length*.—About 26.0 to 34.0 millimeters.

*Diameter*.—About 2.0 millimeters.

*Color*.—Upper surface orange (RHS GREYED ORANGE 166 A). Lower surface light green (RHS YELLOW GREEN N 144 A or RHS YELLOW GREEN N 144 B).

*Ratio blade length/petiole length*.—More or less 5.30.

Leaf glands:

*Size*.—Considered medium. Their length is about 2.0 millimeters.

*Number*.—Generally 2.

*Type*.—Round.

*Color*.—Red (RHS RED GROUP 46 A).

*Diameter*.—Approximately 2.0 millimeters.

Leaf stipules:

*Generally*.—No leaf stipules were observed.

Flowers:

Flower buds:

*Generally*.—At pre-floral stage of development, the floral bunches are make up with 3 to 4 floral buds having a conic shape with a round tip. Their form is evolving until blooming, with variables dimensions. Just before blooming, floral buds have a diameter of about 9.5 millimeters wide and are approximately 18.0 millimeters long.

*Color*.—This characteristic is dependent upon the proximity to bloom. At pre-floral stage of development, the bottom of the flowers buds, or calyx formed by sepals, is of light green color (RHS YELLOW GREEN 144 A to RHS YELLOW GREEN 144 B) with purple pink areas (RHS GREYED RED GROUP 178 A to RHS GREYED RED GROUP 178 B); the corolla formed by petals, is generally pure white (RHS WHITE 155 D) on both upper and lower surfaces.

*Hardiness*.—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom*.—Generally late March. The first bloom was observed on March 5$^{th}$ until Mar. 15, 2010. Last fifth blooms took place respectively from March 23$^{rd}$ until Apr. 1, 2011, from April 6$^{th}$ to Apr. 16, 2013, from March 23$^{rd}$ to Apr. 2, 2014, from April 2$^{nd}$ to Apr. 12, 2015 and then from March, 31$^{st}$ to Apr. 11, 2016.

*Blooming time*.—Considered medium relative comparison to other commercial cherry cultivars grown in the Pyrénées-Orientales department, France. The date of full bloom is observed at the middle of the blooming period. The date of bloom varies slightly with climatic conditions and cultural practices.

*Blooming period*.—Average 10 days. This characteristic varies slightly with the prevailing climatic conditions.

*Flower type*.—The variety is considered to have a showy type flower.

*Flower size*.—Considered large. Average diameter between 30.0 and 37.0 millimeters when totally opened.

*Bloom quantity*.—Considered abundant, approximately 60 flowers per meter.

*Flower bud frequency*.—Generally 4 to 8 flower buds appear per node.

Petal:

*Size*.—Considered medium for the species.

*Length*.—Generally about 17.0 to 19.0 millimeters.

*Width*.—Generally about 16.0 to 19.0 millimeters.

*Petal form*.—Large form, elliptic, usually slightly overlapping.

*Petal count*.—Nearly always 5.

*Petal texture*.—Both petal surfaces have a smooth and soft texture.

*Petal color*.—Pure white color (RHS WHITE 155 D) on both surfaces.

*Fragrance*.—Very soft.

*Petal base descriptor*.—The base of the petal is narrower than the rest of the petal, and slightly pointed.

Petal claw:

*Form*.—The claw is considered to have a conic form with a slightly rounded tip.

*Length*.—Approximately 7.0 millimeters.

*Width*.—Approximately 4.0 millimeters.

*Petal margins*.—Smooth and slightly wavy.

Petal apex:

*Generally*.—The petal apices are generally wide dome shaped.

Flower pedicel:

*Length*.—Considered medium to long and having an average length of approximately 16.0 to 22.0 millimeters.

*Diameter*.—Average 1.4 millimeter.

*Color*.—Green (RHS YELLOW GREEN 144 A to RHS YELLOW GREEN B).

Calyx:

*Internal surface texture*.—Smooth texture.

*Color*.—The upper surface is of light green color (RHS YELLOW GREEN 144 A to RHS YELLOW GREEN 144 B) with purple pink areas (RHS GREYED RED GROUP 178 A to RHS GREYED RED GROUP 178 B). The lower surface is of light green color (RHS YELLOW GREEN 144 B to RHS YELLOW GREEN 144 C or RHS YELLOW GREEN 151 A to RHS YELLOW GREEN 151 B).

Sepals:

*Surface texture*.—The outer and inner surfaces of the sepals have a smooth texture.

*Size*.—Usually considered medium.

*Length*.—Approximately 6.0 millimeters.

*Width*.—Approximately 4.8 millimeters.

*Shape*.—Elliptic shape.

*Color*.—The upper surface is green (RHS YELLOW GREEN 144 A to RHS YELLOW GREEN 144 B) with pink purple zones (RHS GREYED RED 178 A to RHS GREYED RED 178 B). The sepal under surface is of light green color (RHS YELLOW GREEN 144 B to RHS YELLOW GREEN 144 C or RHS YELLOW GREEN 151 A to RHS YELLOW GREEN 151 B).

*Number of sepals*.—Generally 5.

*Sepal apex and margin descriptors*.—Elliptic in shape with a slightly rounder apex.

*Average number of stamens per flower*.—Between 36 and 40 stamens per flower.

*Stamen*.—Size compared to petals. The size of stamen is smaller than the size of petals.

Anthers:

*Length*.—Medium. Approximately 12.0 millimeters.

*Form*.—Cardioid.

*Color*.—Yellow orange red color (RHS GREYED ORANGE 163 B to RHS GREYED ORANGE 163 C). The color evolves with flowering.

*Pollen production*.—Pollen is abundant, and has a yellow color (RHS YELLOW ORANGE 17 B to RHS YELLOW ORANGE 17 Cor RHS YELLOW ORANGE 9 A) that varies with maturity. The fertility has been checked and the 'REDLAM' variety is not self-fertile (or self pollinating). However, because of the considerable amount of pollen that is product, the pollination is performed as expected.

Filaments:

*Size*.—Variable in length, approximately between 8.0 and 10.0 millimeters in length, smaller than pistil's length.

*Color*.—Considered as white (RHS WHITE 155 D).

Pistil:

*Number*.—Usually 1.

*Length*.—Approximately from 15.0 to 17.0 millimeters including the ovary, that is longer than stamens length.

*Color*.—Considered very pale green (RHS YELLOW GREEN 149 B to RHS YELLOW GREEN 149 C). The color is evolving with flowering.

*Surface texture*.—Glabrous.

*Pubescence*.—Absent.

*Stigma*.—Approximately 1.1 millimeter in diameter, with an elliptic shape and a light green color (RHS YELLOW GREEN N 144 A to RHS YELLOW GREEN N 144 B).

*Ovary*.—Approximately 2.8 millimeters in height. The diameter of the ovary is about 1.9 millimeters.

*Ovary color*.—The ovary color is green (RHS GREEN 143 A).

Type of reproduction: Pollination.

Pollinator: Good pollinators are the following varieties: 'ROSILAM' cherry tree (U.S. Plant Pat. No. 23,797) or 'RUBILAM' cherry tree (U.S. Plant Pat. No. 23,798).

Fruits:

*Maturity when described*.—Firm at maturity.

*Date of first picking*.—May 18, 2009. The date of picking varies slightly with climatic conditions.

*Date of last picking*.—Last known picking times carry on from May 18$^{th}$ to May 25, 2009, then from May 30$^{th}$ to Jun. 1, 2010, then from May 19$^{th}$ to May 26, 2011, then from May 24$^{th}$ to Jun. 4, 2012, then from June 7$^{th}$ to Jun. 14, 2013, then from May 14$^{th}$ to May 20, 2014 and then from May 24$^{th}$ to May 28, 2015 and then from June 1$^{st}$ to Jun. 5, 2016.

*Ripening period*.—Approximately 5 to 12 days.

Size:

*Generally*.—Considered medium to large, with a homogeneous size between them.

*Average cheek diameter*.—About 29.0 to 31.0 millimeters.

*Average axial diameter*.—About 21.0 to 24.0 millimeters.

*Typical weight*.—Generally about 11.6 grams. This characteristic is highly dependent upon the prevailing cultural practices, and therefore is not particularly distinctive of the variety.

Fruit form:

*Generally*.—Reniform.

*Fruit suture*.—Wide mouthed, extending from the base to the apex. No apparent callousing or stitching exists along the suture line. Without mucrons and not prominent.

Suture:

*Color*.—The suture has generally a color similar to the blush fruit color, a homogenous dark red color (RHS RED GROUP 46 A).

Ventral surface:

*Form*.—Smooth.

*Apex*.—Round with a slight depression.

*Base*.—Slightly in depression.

*Stem cavity*.—Average depth of the stem cavity is about 2.0 to 3.0 millimeters. Average width is about 6.0 millimeters.

Fruit skin:

*Thickness*.—Considered smooth and medium thick, and tenacious to the flesh depending on stage of maturity.

*Tenacity*.—Tenacious to flesh.

*Texture*.—Smooth.

*Taste*.—Sweet.

*Tendency to crack*.—None.

Color:

*Blush color*.—The color of the fruit is red (RHS GREYED PURPLE 187 B) on a dark red color red (RHS RED GROUP 46 A) background.

*Fruit stem*.—Medium in length, approximately 34.0 to 39.0 millimeters.

*Diameter*.—Approximately 1.5 millimeters.

*Color*.—Light green (RHS YELLOW GREEN 145 A).

Flesh:

*Ripens*.—Homogenous and regular.

*Texture*.—Very crunchy, luscious, juicy.

*Fibers*.—No fibers.

*Firmness*.—Considered firm.

*Aroma*.—Pronounced aroma.

*Eating quality*.—Very good, very sweet, aromatic.

*Flavor*.—Semi-sweet, very sugared, aromatic. Low acidic level. Juicy and aromatic.

*Juice*.—Large amount, very juicy. Color of juice is considered pink red (RHS RED PURPLE 73 D).

*Brix*.—The minimal sugar level is approximately 16.0 degrees, varies slightly with amount of fruit per tree and climatic conditions.

*Color*.—From an orange yellow color (RHS YELLOW ORANGE 14 D) to a pigmented red color (RHS RED GROUP 53 B) at ripening time.

Stone:

*Type*.—Free stone to semi-freestone at fruits picking.

*Size*.—Medium for the variety.

*Length*.—Average 10.0 millimeters.

*Width*.—Average width 9.0 millimeters.

*Diameter*.—Average diameter 7.5 millimeters.

*Form*.—Round.

*Base*.—Generally round.

*Apex*.—Generally round.

*Stone cavity*.—Medium with a form and dimensions corresponding to the stone's dimensions.

Stone surface:

*Surface texture*.—Smooth.

*Ridges*.—None, smooth.

*Tendency to split*.—Splitting is absent.

Ventral edge:

*Width*.—Very shallow, more or less 1.0 millimeter.

Dorsal edge:

*Shape*.—Full, with a slight relief.

*Stone color*.—The color of the dry stone is yellow (RHS GREYED YELLOW 161 D).

*Tendency to split*.—None.

Kernel:

*Size*.—Medium.

*Length*.—About 7.0 millimeters.

*Width*.—About 5.0 millimeters.

*Thickness*.—About 3.5 millimeters.

*Form*.—Round to slightly elliptic.

*Pellicle*.—Not pubescent.

*Color*.—The kernel skin is orange brown (RHS GREYED YELLOW 161 C). The kernel and its embryo are mature at the time of fruit maturity.

Use: Dessert. Fresh products.

*Market*.—Local and long distance. On the tree fruits can stay 10 days while keeping good gustative qualities. The lifetime after picking is also good.

Keeping quality: Good, held well for 30 days in cold storage at 2° C. and maintained good appearance and eating quality.

Shipping quality: Good, showed minimal bruising or scarring during picking, packing and shipping trials.

Plant/fruit disease resistance/susceptibility: Specific tests were run with regards to *Monilia* and 'REDLAM' variety seems to be low sensitive to *Monilia*. Moreover 'REDLAM' is low sensitive to other observed pathologies, to rupture and to conservation pathologies.

The present new variety of cherry tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of cherry tree, substantially as illustrated and described, characterized by its fruit and especially by its medium to large size, its dark red skin color, its firmness, good flavor and eating quality; the fruit is further characterized by its good handling and storage qualities.

* * * * *